United States Patent

Rahman et al.

[11] Patent Number: 5,552,066
[45] Date of Patent: Sep. 3, 1996

[54] RIBOSE DIESTER QUATERNARY USEFUL AS A FABRIC CONDITIONER

[75] Inventors: Mohammad A. Rahman, River Edge, N.J.; Anthony Hung, New City, N.Y.; Shang-Ren Wu, Mahwah, N.J.

[73] Assignee: Lever Brothers Company, Division of Conopco, Inc., New York, N.Y.

[21] Appl. No.: 393,626

[22] Filed: Apr. 14, 1995

Related U.S. Application Data

[63] Continuation-in-part of Ser. No. 252,033, Jun. 1, 1994, Pat. No. 5,429,756.

[51] Int. Cl.$^6$ .................. D06M 13/322; D06M 13/46; C07D 307/02
[52] U.S. Cl. .................. 252/8.63; 252/8.86; 252/8.91; 549/478
[58] Field of Search .................. 252/8.6, 8.7, 8.75, 252/8.8; 549/478

[56] References Cited

U.S. PATENT DOCUMENTS

| | | | |
|---|---|---|---|
| 4,137,180 | 1/1979 | Naik et al. | 252/8.8 |
| 4,767,547 | 8/1988 | Straathof et al. | 252/8.8 |
| 4,789,491 | 12/1988 | Chang et al. | 252/8.75 |
| 4,913,828 | 4/1990 | Caswell et al. | 252/8.8 |
| 5,254,269 | 10/1993 | Taylor et al. | 252/8.6 |

*Primary Examiner*—Anthony Green
*Attorney, Agent, or Firm*—A. Kate Huffman

[57] ABSTRACT

Biodegradable compounds which are effective fabric conditioning molecules are described as having Formula I

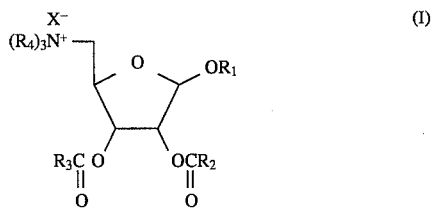

wherein $R_1$ is a $C_{1-4}$ alkyl or alkenyl, $R_2$ and $R_3$ are each independently a $C_7$–$C_{30}$ straight or branched alkyl or alkenyl, $R_4$ is a $C_{1-4}$ alkyl or alkenyl or hydroxyalkyl and X is a water soluble anion.

11 Claims, No Drawings

RIBOSE DIESTER QUATERNARY USEFUL AS A FABRIC CONDITIONER

FIELD OF THE INVENTION

This application is a continuation-in-part of U.S. Ser. No. 08/252,033 filed on Jun. 1, 1994, now U.S. Pat. No. 5,429,756. This invention relates to novel ribose diester quaternary ammonium compounds which are effective fabric conditioners and are aquatically non-toxic.

BACKGROUND OF THE INVENTION

Quaternary ammonium salts such as N,N-di(tallowoyl-oxy-propyl)-N-N-dimethyl ammonium methyl sulfate are known as effective fabric conditioning agents which are also readily biodegradable as described in U.S. Pat. Nos. 4,137,180; 4,767,547 and 4,789,491. The biodegradable cationic diester compounds described in U.S. Pat. No. 4,137,180 are preferred fabric conditioning molecules.

However, it has been observed that some of these fabric conditioning molecules degrade by hydrolization of one of the ester moieties from the molecule which may result in a monoester which may cause aquatic toxicity.

Therefore, there is a need for novel molecules which are both effective fabric conditioners and which biodegrade into environmentally friendly forms.

SUMMARY OF THE INVENTION

It is thus an object of the invention to provide novel compounds which are both effective fabric conditioners and which hydrolyze to form non-toxic moieties.

Another object is to provide novel ribose diester quaternary ammonium compounds which are effective fabric conditioners useful for fabric softening and static control in a variety of stable physical forms.

A further object of the invention is to provide environmentally friendly fabric conditioning compositions which are also effective fabric conditioners.

Another object is to provide a process for laundering fabrics which yield good fabric conditioning using the novel biodegradable molecules of the invention.

DETAILED DESCRIPTION OF PREFERRED EMBODIMENTS

The present invention relates to novel aquatically non-toxic cationic fabric conditioning agents having a Formula I

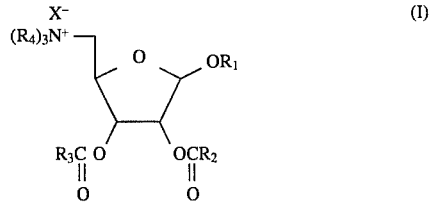

wherein $R_1$ is a $C_{1-4}$ alkyl or alkenyl, $R_2$ and $R_3$ are each independently a $C_7$–$C_{30}$ straight or branched alkyl or alkenyl, $R_4$ is a $C_{1-4}$ alkyl, alkenyl or hydroxyalkyl and $X^-$ is a water soluble anion.

Preferably, $R_1$ and $R_4$ are each a $C_{1-4}$ alkyl and $R_2$ and $R_3$ are each a $C_{15-28}$ straight or branched chain alkyl.

The term "water soluble" means that the cationic compounds of Formula I remain dispersed throughout the laundry solution during the washing process.

The anion $X^-$ in the molecule is preferably the anion of a strong acid and can be, for example, chloride, bromide, iodide, sulfate and methyl sulfate; the anion may carry a double charge in which case $X^-$ represents half a group.

Preferred compounds of Formula I include β-methyl-2,3-dipalmitoyl-5-deoxy-trimethylammonium-D-ribofuranoside methyl sulfate.

Preparation

A concentrated acid was added to a solution of D-ribose in short chain alcohol at 0° C. to 20° C. and stirred for four to six days. The resulting solution was neutralized and the solvent was removed. The residue was then added to a solution of p-toluene sulfonyl chloride in anhydrous pyridine. The resulting compound was mixed with tetrahydrofuran and a dialkyl amine, at a temperature of from about 40° C. to about 60° C. for about one to three days. The resulting product was added to a solution of a long chain fatty acid in a suitable solvent and anhydrous pyridine. The products are isolated as waxy materials. The desired product was obtained by quaternization with alkyl chloride ($C_1$–$C_4$) or alkyl methyl sulfate ($C_2$–$C_4$). Suitable solvents include methylene chloride, toluene, and xylene. Long chain amines which can be used are dihexadecyl amine up to 30 carbons and mixtures of different chains. Long chain esters of amines are also possible by reacting diethanolamine with nicotinic and then reacting with long chain fatty acids.

The fabric conditioning compositions comprise an effective amount of Formula I, preferably from about 5 to about 99 wt. %, more preferably from about 10 to about 95 wt. %, most preferably from about 15 to about 90 wt. %.

The fabric conditioning compositions may be formulated in a variety of physical forms such as liquid, paste, tumble dryer sheets, flakes or granules. The compositions may also be combined with detergent formulations to provide a laundry detergent which also conditions fabrics.

Additional Fabric Conditioning Agents

The novel compounds of the invention may also be combined with hydrocarbon fabric agents known in the art to form an active mixture. Preferably, the hydrocarbon softeners are biodegradable.

Examples of such agents include cationic quaternary ammonium salts, tertiary fatty amines, carboxylic acids, esters of polyhydric alcohols, fatty alcohols, ethoxylated fatty alcohols, ethoxylated fatty amines, ethoxylated monoglycerides and ethoxylated diglycerides, mineral oils and polyols such as polyethyleneglycol, and silicone oils as described in U.S. Pat. No. 5,254,269 (Taylor et al.).

Optional Ingredients

Other optional ingredients which may be included in the fabric conditioning compositions of the invention include optical brighteners or fluorescent agents, perfumes, colorants, germicides and bactericides, each optional additive being present in an amount of up to about 10 wt. %.

Detergent Formulations

The conditioning compositions of the present invention can be incorporated into both granular and liquid detergent formulations with little detrimental effect on cleaning.

The compositions are typically used at levels up to about 30% of the detergent composition, preferably from about 5 to 20% of the composition.

Detergent Surfactant

Detergent surfactants included in the detergent formulations of the invention may vary from 1% to about 99% by weight of the composition depending on the particular surfactant(s) used and the cleaning effects desired.

Preferably, the surfactant is present in an amount of from about 10 to 60% by weight of the composition. Combinations of anionic, preferably alkyl sulfates, alkyl ethoxylated sulfates, linear alkyl benzene sulfonates, and nonionic, preferably alkyl polyethoxylated alcohol surfactants are preferred for optimum cleaning, softening and antistatic performance. It may be appreciated that other classes of surfactants such as ampholytic, zwitterionic or cationic surfactants may also be used as known in the art. As generally known, granular detergents incorporate the salt forms of the surfactants while liquid detergents incorporate the acid form where stable. Examples of surfactants within the scope of the invention are described in U.S. Pat. No. 4,913,828 issued to Caswell et al., herein incorporated by reference.

Builders, accumulating agents and soil release agents known in the art may also be used in the detergent formulations. Examples of such suitable components are described in Caswell et al., U.S. Pat. No. 4,913,828, herein incorporated by reference.

Other Optional Detergent Ingredients

Optional ingredients for the detergent compositions of the present invention other than those discussed above include hydroropes, solubilizing agents, suds suppressors, soil suspending agents, corrosion inhibitors, dyes, fillers, optical brighteners, germicides, pH adjusting agents, enzyme stabilizing agents, bleaches, bleach activators, perfumes and the like.

EXAMPLES

Example 1

β-methyl-2,3-dipalmitoyl-5-deoxy-trimethylammonium-D-ribofuranoside methyl sulfate is prepared as follows.

To a solution of D-Ribose (80 g, 0.5 mol) in anhydrous methanol (800 ml) in a 2 liter three-neck jacketed round-bottom flask was added concentrated sulfuric acid (8–10 ml) at 0°–5° C. and stirred the reaction mixture for four days. Then the solution was neutralized with basic ion exchange resin. The resin was filtered off and the solvent was removed on a rotary evaporator which gave the β-methyl-D-ribofuranoside product. The pure β-isomer was obtained by crystallization from ethyl acetate, m.p. 79°–80° C. The compound showed the following characteristics: $^1$H NMR (200 MHz, D$_2$O) δ 3.40 (s, 3H, OCH), 3.62 (dd, 1H, H-5), 3.83 (dd, 1H, H-5), 4.05 (m, 3H, H-2, H-4, OH), 4.14 9s, 1H, OH), 4.17 (dd, 1 H, H-3), 4.91 (s, 1 H, H-1 ).

To a solution of β-methyl-D-ribofuranoside (10 g, 0.304 mol) ion anhydrous pyridine (10 ml) in a 100 ml three-neck round-bottom flask fitted with a condenser and nitrogen inlet adapter a solution of tosyl chloride (12.58 g, 0.066 mol) in anhydrous pyridine (50 ml) was added dropwise at 0° C. under nitrogen atmosphere. The reaction mixture was stirred at 0° C. for 3 hours and then at room temperature for three days. The excess pyridine was removed under reduced pressure which gave the crude product (15 g, 70% yield). The compound β-methy-5-O-toluenesulfonyl-D-ribofuranoside showed the following characteristics: $^1$H NMR (200 MHz, d$_6$-acetone) δ 2.45 (s, 3H, CH$_3$), 3.28 (s, 3H, OCH$_3$), 2.87 ( d, 1 H, H-5), 4.02 (m, 4H, H-5, H-2, H-4, OH), 4.23 (m, 2H, H-3, OH), 4.71 (s, 1H, H-1), 7.51, 7.86 (ABq, 4H, C$_6$H$_4$).

β-methyl-5-O-toluenesulfonyl-D-ribofuranoside (13.43 g, 0.042 mol) was added to anhydrous tetrahydrofuran (40 ml) in a pressure reactor). Dimethylamine was condensed (8 ml) using a dry ice condenser and added quickly to the reactor. Immediately the pressure reactor was closed and placed in an oil bath at 50° C. for two days. The excess dimethylamine was removed by passing nitrogen through the reactor and then the tetrahydrofuran was removed on a rotary evaporator which gave the crude product (6.8 g, 85% yield). 5-N,N-dimethylamino-β-D-methylribofuranoside showed the following characteristics: $^1$H NMR (200 MHz, CD$_3$OD) δ 2.87 (s, 6H, CH$_3$), 3.45 (s, 3H, OCH$_3$), 3.89 (d, 2H, H-5), 4.02 (dd, 2H, H-2, H-4), 4.19 (m, 2H, H-3, OH), 4.79 (s) 1H, H-1), MS (Cl, isobutane), MH$^+$, 192.

To a solution of β-methyl-5-deoxy-N,N-dimethylamino-D-ribofuranoside (1.32 g, 0.007 mol) in anhydrous methylene chloride (50 ml) in a 500 ml three-neck round-bottom flask was added a solution of palmitoyl chloride (2.89 g, 0.011 mol)in methylene chloride (10 ml) and anhydrous pyridine (1 ml). The reaction mixture was stirred at 0° C. for 3 hours and then at room temperature overnight. Then the reaction mixture was extracted with methylene chloride (3×100 ml), washed with brine (3×20 ml) and dried over anhydrous sodium sulfate. After filtration the solvent was removed on a rotary evaporator which gave the crude product (4.2 g, 90% yield). The crude product was purified on a silica gel column eluting first with hexane: ethyl acetate (1:1) and then with chloroform:methanol (9:1). The solvent was removed on a rotary evaporator which gave the β-methyl-2,3-dipalmitoyl- 5-deoxy-N,N-dimethylamino-D-ribofuranoside. The compound showed the following characteristics: $^1$H NMR (200 MHz, CDCl$_3$) δ 0.88 (t, 6H, CH$_3$), 1.26 (br, 48H, CH$_2$), 1.62 (t, 4H, CH$_2$), 2.32 (t, 4H, CH$_2$), 2.94, 3.01 (2s, 6H, CH$_3$), 3.36 (s, 3H, OCH), 4.09 (m, 3H, H-2, H-3, H-4), 4.82 (s, 1H, H-1), 5.16 (m, 2H, H-5), $^{13}$C NMR (50 MHz, CDCl$_3$) δ 14.14, 22.65, 22.73, 22.80, 24.81, 24.97, 25.23, 28.73, 29.09, 29.16, 29.27, 29.35, 29.41, 29.55, 29.73, 29.82, 29.88, 31.89, 31.96, 32.02, 33.45, 34.02, 34.07, 35.35, 45.59, 45.66, 45.73, 55.19, 63.42, 73.46, 78.90, 106.46, 172.46, 172.58, MS (Cl, isobutane), MH$^+$ 668.

To a solution of β-methyl-2,3-dipalmitoyl-5-deoxy-N,N-dimethylamino-D-ribofuranoside (0.647 g, 0.001 mol) in anhydrous toluene (5 ml) in a 100 ml two-neck round-bottom flask was added dimethylsulfate dropwise at room temperature. The reaction mixture was stirred at room temperature overnight. The solid was removed by filtration and then recrystallized from diethylether which gave β-methyl-2,3-dipalmitoyl-5-deoxy-trimethylammonium-D-ribofuranoside (0.75 g, 95% yield) m.p. 79°–81° C. The compound showed the following characteristics: $^1$H NMR (200 MHz, CDCl$_3$) δ 0.85 (t, 6H, CH$_3$), 1.26 (br, 48H, CH$_2$), 1.59 (m, 4H, CH$_2$), 2.33 (m, 4H, CH$_2$), 3.40 (s, 9H, CH$_3$), 3.43 (s, OCH$_3$), 4.91 (s, 1H, H-1), 5.18–5.26 (m, 2H, H-2, H-3), 13C NMR (50 MHz, CDCl$_3$) δ 14.13, 22.71, 29.38, 29.73, 33.91,54.33, 56.21, 69.58, 72.51, 72.88, 74.72, 107.46, 172.32, 162,91, MS (FAB), C$^+$, 668.

Example 2

A fabric conditioning composition containing the ribose diester quaternary compound of Example 1 was prepared. A 5% dispersion of the ribose diester quaternary was prepared by adding the active to demineralized water and heating the mixture to 75° C. to form a homogeneous dispersion (Sample A).

A 5% dispersion of N,N-di(tallowoyl-oxy-propyl)-N,N-dimethyl ammonium methyl sulfate was also prepared under the same procedure (Sample B).

Example 3

To evaluate the softening performance of the novel compound, two grams of each of Samples A and B were separately added to a liter of tap water at ambient temperature containing 0.001% by weight of sodium alkyl benzene sulfonate to simulate carryover of anionic detergent active from the wash. 800 ml of the obtained solution of each sample were put in a Tergotometer pot and four pieces of terry towel (40 grams total weight) were added. The cloths were treated for five minutes at 60 rpm, spun dried and line dried. The dried fabrics were assessed for softness by an expert panel using a round-robin test protocol which assigned a number for softness performance.

Softness performance by softness scale was as follows:

TABLE 1

| Sample A | 2.5 |
|---|---|
| Sample B | 3.5 |

The softening performance of the ribose diester quaternary compound was comparable to that of the prior art compound of Sample B. Thus, the ribose diester quat shows a good softening effect on fabric.

Example 4

The biodegradability of the compound of Example 1 was evaluated by a modified Sturm test and found to exhibit 59% degradation.

The Modified Sturm Test Procedure

The Modified Sturm Test was adopted by the OECD on May 12, 1981 and renamed as the 301 B $CO_2$ Evolution Test in early 1993, herein incorporated by reference.

A high biodegradation result in this test provides the evidence that the test compound is highly biodegradable in aerobic systems.

The test is started by bubbling $CO_2$-free air through the solution at a rate of 50–100 ml/min per carboy (approximately 1–2 bubbles/second). The $CO_2$ produced in each carboy reacts with the barium hydroxide and is precipitated out as barium carbonate; the amount of $CO_2$ produced is determined by titrating the remaining $Ba(OH)_2$ with 0.05N standardized HCl (see below). Periodically (every 2 or 3 days), the $CO_2$ absorber nearest the carboy is removed for titration. The remaining two absorbers are each moved one place closer to the carboy, and a new absorber filled with 100 ml of fresh 0.025N $Ba(OH)_2$ is placed at the far end of the series. Titrations are made as needed (before any $BaCO_3$ precipitate is evident in the second trap), approximately every other day for the first 10 days, and the every fifth day until the 28th day.

For water-insoluble test materials, incorporated dry into the $CO_2$ test carboy, agitation can be done with a magnetic stirrer. For foaming chemicals, $CO_2$ test carboy, agitation can be done with a magnetic stirrer. For foaming chemicals, $CO_2$-free air bubbling can be replaced by overhead aeration and magnetic stirring.

On the 26th day, the pH of the carboy contents is measured again, and then 1 ml of concentrated HCl is added to each of the test carboys to drive off inorganic carbonate. The carboys are aerated overnight, and samples are removed from each carboy for dissolved organic carbon (DOC) analysis. The final titration is made on day 28.

Titrations of the 100-ml $Ba(OH)_2$ solution are made after removing the bottles closest to the carboys. The $Ba(OH)_2$ is titrated with 0.05N HCl, using phenophthalein as an indicator.

The test is run at room temperature and temperature is recorded during the test period.

Theoretical amount of $CO_2$ is compared to amount of $CO_2$ produced to determine the biodegradation of a test material.

We claim:

1. A compound having a Formula I wherein $R_1$ is a $C_{1-4}$ alkyl or alkenyl, $R_2$ and $R_3$ are each independently a $C_7$–$C_{30}$ straight or branched alkyl or alkenyl, $R_4$ is a $C_{1-4}$ alkyl or alkenyl or hydroxyalkyl and $X^-$ is a water soluble anion.

2. The compound according to claim 1 wherein $R_1$ and $R_4$ are each a $C_{1-4}$ alkyl and $R_2$ and $R_3$ are each a $C_{15-28}$ straight or branched chain alkyl.

3. The compound according to claim 2 wherein $R_4$ is methyl.

4. The compound according to claim 1 wherein X is selected from the group consisting of a halide, a sulfate and a nitrate.

5. The compound according to claim 4 wherein X is selected from a group consisting of a chloride, a bromide, an iodide and a methyl sulfate.

6. The compound according to claim 1 wherein the compound is β-methyl-2,3-dipalmitoyl-5-deoxy-trimethyl ammonium-D-ribofuranoside methyl sulfate.

7. A fabric conditioning composition comprising:

about 1 to about 99 wt. % of a compound having a Formula I wherein $R_1$ is a $C_{1-4}$ alkyl or alkenyl, $R_2$ and $R_3$ are each independently a $C_7$–$C_{30}$ straight or branched alkyl or elkenyl, $R_4$ is a $C_{1-4}$ alkyl or alkenyl or hydroxyalkyl and X is a water soluble anion; and about 99 wt. % to about 1 wt. % water.

8. The composition according to claim 7 wherein the composition comprises from about 15 to about 90 wt. % of the compounds of Formula I.

9. The composition according to claim 7 further comprising a hydrocarbon fabric conditioner active.

10. The composition according to claim 7 wherein the composition further comprises at least one additive selected from the group consisting of an optical brightener, a fluorescent agent, a perfume, a colorant, a germicide, a bactericide and mixtures thereof, the amount of each additive being up to about 10 wt. %.

11. The composition according to claim 7 wherein the compound of Formula I is β-methyl-2,3-dipalmitoyl-5-deoxy-trimethyl ammonium-D-ribofuranoside methyl sulfate.

* * * * *